US009023255B2

(12) United States Patent
Bricker et al.

(10) Patent No.: US 9,023,255 B2
(45) Date of Patent: May 5, 2015

(54) PRODUCTION OF NITROGEN COMPOUNDS FROM A METHANE CONVERSION PROCESS

(71) Applicant: UOP LLC, Des Plaines, IL (US)

(72) Inventors: Jeffery C. Bricker, Buffalo Grove, IL (US); John Q. Chen, Glenview, IL (US); Peter K. Coughlin, Mundelein, IL (US); Debarshi Majumder, Forest Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/915,106

(22) Filed: Jun. 11, 2013

(65) Prior Publication Data
US 2014/0056803 A1    Feb. 27, 2014

Related U.S. Application Data

(60) Provisional application No. 61/691,371, filed on Aug. 21, 2012.

(51) Int. Cl.
*C09B 63/00* (2006.01)
*C07D 213/12* (2006.01)
*C07C 253/18* (2006.01)
*C07D 207/06* (2006.01)
*C07D 201/08* (2006.01)
*C01B 3/26* (2006.01)
*C01B 3/02* (2006.01)
*C01B 3/36* (2006.01)

(52) U.S. Cl.
CPC ............ *C07D 213/12* (2013.01); *C07C 253/18* (2013.01); *C07D 207/06* (2013.01); *C07D 201/08* (2013.01); *C01B 3/26* (2013.01); *C01B 3/025* (2013.01); *C01B 3/36* (2013.01); *C01B 2203/025* (2013.01); *C01B 2203/04* (2013.01); *C01B 2203/048* (2013.01); *C01B 2203/068* (2013.01)

(58) Field of Classification Search
USPC ........................................................ 546/253
See application file for complete search history.

(56) References Cited

U.S. PATENT DOCUMENTS

| | | | |
|---|---|---|---|
| 748,091 A | 12/1903 | Nethery | |
| 2,581,102 A | 1/1952 | Hodges | |
| 2,822,410 A | 2/1958 | Wojcik et al. | |
| 2,934,537 A * | 4/1960 | Cislak et al. | 546/253 |
| 3,264,307 A * | 8/1966 | Jones et al. | 546/253 |
| 3,565,940 A | 2/1971 | Brown et al. | |
| 3,615,164 A | 10/1971 | Baker et al. | |
| 3,816,975 A | 6/1974 | Collins | |
| 4,009,219 A | 2/1977 | Tamers | |
| 4,094,777 A | 6/1978 | Sugier et al. | |
| 4,136,015 A | 1/1979 | Kamm et al. | |
| 4,181,662 A | 1/1980 | Sweeney | |
| 4,191,636 A | 3/1980 | Fukui et al. | |
| 4,288,641 A | 9/1981 | Codignola et al. | |
| 4,356,124 A | 10/1982 | Pesa et al. | |
| 4,357,228 A | 11/1982 | Che | |
| 4,387,263 A | 6/1983 | Vogt et al. | |
| 4,426,248 A | 1/1984 | Jackson | |
| 4,493,715 A | 1/1985 | Hogan et al. | |
| 4,544,792 A | 10/1985 | Smith et al. | |
| 4,587,373 A | 5/1986 | Hsia | |
| 4,724,272 A * | 2/1988 | Raniere et al. | 585/500 |
| 4,744,221 A | 5/1988 | Knollmueller | |
| 4,892,567 A | 1/1990 | Yan | |
| 4,929,789 A | 5/1990 | Gupta et al. | |
| 5,026,935 A | 6/1991 | Leyshon et al. | |
| 5,095,163 A | 3/1992 | Barger | |
| 5,096,470 A | 3/1992 | Krishnamurthy | |
| 5,126,308 A | 6/1992 | Barger et al. | |
| 5,191,141 A | 3/1993 | Barger et al. | |
| 5,219,530 A | 6/1993 | Hertzberg et al. | |
| 5,227,570 A | 7/1993 | Tan | |
| 5,232,474 A | 8/1993 | Jain | |
| 5,276,257 A | 1/1994 | Diesen | |
| 5,278,344 A | 1/1994 | Gosling et al. | |
| 5,300,216 A | 4/1994 | Hertzberg et al. | |
| 5,419,884 A | 5/1995 | Weekman et al. | |
| 5,446,232 A | 8/1995 | Chen et al. | |
| 5,478,950 A | 12/1995 | Bergfeld et al. | |
| 5,482,616 A | 1/1996 | Brahma et al. | |
| 5,510,565 A | 4/1996 | Tan et al. | |
| 5,760,266 A | 6/1998 | Eaton et al. | |
| 5,990,372 A | 11/1999 | Blankenship et al. | |
| 6,049,011 A | 4/2000 | Kiss et al. | |
| 6,190,623 B1 | 2/2001 | Sanger et al. | |
| 6,210,791 B1 | 4/2001 | Skoog et al. | |
| 6,278,033 B1 | 8/2001 | Flick et al. | |
| 6,395,197 B1 | 5/2002 | Detering et al. | |
| 6,442,931 B1 | 9/2002 | Vasin et al. | |
| 6,443,354 B1 | 9/2002 | Plochl et al. | |
| 6,465,701 B1 | 10/2002 | Marsella et al. | |
| 6,478,535 B1 | 11/2002 | Chung et al. | |
| 6,610,124 B1 | 8/2003 | Dolan et al. | |

(Continued)

FOREIGN PATENT DOCUMENTS

| | | |
|---|---|---|
| BY | 7932 C1 | 4/2006 |
| CA | 2391441 A1 | 6/2001 |

(Continued)

OTHER PUBLICATIONS

Natural Gas.*

(Continued)

*Primary Examiner* — Brandon Fetterolf
*Assistant Examiner* — Blaine G Doletski

(57) ABSTRACT

Methods and systems are provided for converting methane in a feed stream to acetylene. The hydrocarbon stream is introduced into a supersonic reactor and pyrolyzed to convert at least a portion of the methane to acetylene. The reactor effluent stream may be treated to convert acetylene to nitrogen based hydrocarbon compounds such as pyridines. The method includes the reaction of acetylene with ammonia and controlling the ratio of acetylene to ammonia to generate the desired nitrogen based hydrocarbon compound.

12 Claims, 2 Drawing Sheets

(56) References Cited

U.S. PATENT DOCUMENTS

| | | |
|---|---|---|
| 6,688,100 B1 | 2/2004 | Wherley et al. |
| 6,695,077 B2 | 2/2004 | Szymocha et al. |
| 6,761,777 B1 | 7/2004 | Radon |
| 6,764,602 B2 | 7/2004 | Shutt et al. |
| 6,821,500 B2 | 11/2004 | Fincke et al. |
| 6,953,867 B2 | 10/2005 | Cockman et al. |
| 6,962,199 B1 | 11/2005 | Tjeenk Willink |
| 7,000,306 B2 | 2/2006 | Rice et al. |
| 7,045,670 B2 | 5/2006 | Johnson et al. |
| 7,183,451 B2 | 2/2007 | Gattis et al. |
| 7,208,647 B2 | 4/2007 | Peterson et al. |
| 7,211,128 B2 | 5/2007 | Thomas et al. |
| 7,253,328 B2 | 8/2007 | Stauffer |
| 7,442,350 B1 | 10/2008 | Vanden Bussche |
| 7,655,135 B2 | 2/2010 | Havlik et al. |
| 7,667,085 B2 | 2/2010 | Gattis et al. |
| 7,692,051 B2 | 4/2010 | Johnson et al. |
| 7,744,763 B2 | 6/2010 | Cross et al. |
| 7,759,288 B2 | 7/2010 | Prichett et al. |
| 7,759,531 B2 | 7/2010 | Pinkos et al. |
| 7,763,163 B2 | 7/2010 | Koseoglu |
| 7,901,486 B2 | 3/2011 | Cross et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,919,431 B2 | 4/2011 | Johnson et al. |
| 8,013,196 B2 | 9/2011 | Mamedov et al. |
| 8,013,197 B2 | 9/2011 | Peterson et al. |
| 8,080,697 B2 | 12/2011 | Lin et al. |
| 8,088,962 B2 | 1/2012 | Klanner et al. |
| 8,137,476 B2 | 3/2012 | Morrow et al. |
| 8,211,312 B2 | 7/2012 | Stewart et al. |
| 2002/0154741 A1 | 10/2002 | Rigali et al. |
| 2004/0079228 A1 | 4/2004 | Wijmans et al. |
| 2005/0070748 A1 | 3/2005 | Ellis et al. |
| 2006/0283780 A1 | 12/2006 | Spivey et al. |
| 2007/0018038 A1 | 1/2007 | Jarmon et al. |
| 2007/0149807 A1 | 6/2007 | Dieterle et al. |
| 2007/0191664 A1 | 8/2007 | Hershkowitz et al. |
| 2009/0042998 A1 | 2/2009 | Hashimoto et al. |
| 2010/0005963 A1 | 1/2010 | Snape et al. |
| 2010/0044626 A1 | 2/2010 | Fischer et al. |
| 2010/0126909 A1 | 5/2010 | Bhasin et al. |
| 2010/0130803 A1 | 5/2010 | Keusenkothen et al. |
| 2010/0228069 A1 | 9/2010 | Kuznicki et al. |
| 2010/0319536 A1 | 12/2010 | Song et al. |
| 2010/0324299 A1* | 12/2010 | Yoshikawa et al. ......... 546/345 |
| 2011/0071331 A1 | 3/2011 | Basset et al. |
| 2011/0094378 A1 | 4/2011 | Mitariten |
| 2011/0114285 A1 | 5/2011 | Buxbaum |
| 2011/0297269 A1 | 12/2011 | Pilon et al. |
| 2012/0029256 A1 | 2/2012 | Chen et al. |
| 2012/0178833 A1 | 7/2012 | Clomburg, Jr. et al. |

FOREIGN PATENT DOCUMENTS

| | | | |
|---|---|---|---|
| CN | 101928217 A | | 12/2010 |
| CN | 201768561 U1 | | 3/2011 |
| CN | 102247876 A | | 11/2011 |
| DE | 3327000 A1 | | 2/1985 |
| DE | 19626484 A1 | | 1/1998 |
| DE | 10252859 A1 | | 5/2004 |
| EA | 008761 B1 | | 8/2007 |
| EA | 200800261 A1 | | 4/2008 |
| EA | 013242 B1 | | 4/2010 |
| EP | 0039918 A1 | | 11/1981 |
| EP | 011707 B1 | | 9/1982 |
| EP | 0158863 A2 | | 10/1985 |
| EP | 0173501 A2 | | 3/1986 |
| EP | 0263259 A2 | | 4/1988 |
| EP | 1677910 A2 | | 3/2005 |
| EP | 1667949 A2 | | 4/2005 |
| EP | 1678274 A2 | | 4/2005 |
| EP | 1856047 A2 | | 8/2006 |
| EP | 2022772 A1 | | 2/2009 |
| EP | 2224025 A1 | | 9/2010 |
| EP | 2417721 A1 | | 10/2010 |
| EP | 1663918 B1 | | 2/2012 |
| EP | 2049456 B1 | | 3/2012 |
| GB | 283163 A | | 1/1929 |
| GB | 332258 A | | 7/1930 |
| GB | 334193 A | | 8/1930 |
| GB | 451794 A | | 8/1936 |
| GB | 1358862 A | | 7/1974 |
| GB | 2000180 A | | 4/1979 |
| GB | 2220674 A | | 1/1990 |
| JP | 6046976 A | | 3/1985 |
| JP | 60129552 A | | 7/1985 |
| JP | 1132535 A | | 5/1989 |
| JP | 01277196 A | | 11/1989 |
| JP | 2002348580 A | | 12/2002 |
| KR | 2002009748 A | | 2/2002 |
| RU | 2065866 C1 | | 8/1996 |
| RU | 2145952 C1 | | 2/2000 |
| RU | 98101950 A | | 2/2000 |
| RU | 2158747 C1 | | 11/2000 |
| RU | 2170617 C2 | | 7/2001 |
| RU | 2187768 C2 | | 8/2002 |
| RU | 2204434 C2 | | 5/2003 |
| RU | 2222569 C2 | | 1/2004 |
| RU | 2261995 C2 | | 10/2005 |
| RU | 2264855 C2 | | 11/2005 |
| RU | 2346737 C2 | | 2/2009 |
| RU | 2363521 C1 | | 8/2009 |
| RU | 2367668 C2 | | 9/2009 |
| RU | 2373178 C2 | | 11/2009 |
| RU | 2427608 C2 | | 8/2011 |
| RU | 2438083 C2 | | 12/2011 |
| RU | 2440962 C1 | | 1/2012 |
| RU | 2443758 C2 | | 2/2012 |
| RU | 116365 U1 | | 5/2012 |
| RU | 2451658 C2 | | 5/2012 |
| SU | 234422 A1 | | 5/1969 |
| SU | 280739 A1 | | 2/1976 |
| SU | 803969 A | | 2/1981 |
| SU | 392723 A | | 7/1983 |
| SU | 410596 A | | 7/1983 |
| SU | 1613481 A1 | | 12/1990 |
| SU | 1776652 A1 | | 11/1992 |
| SU | 1778146 A1 | | 11/1992 |
| WO | 9109829 A1 | | 7/1991 |
| WO | 9518089 A1 | | 7/1995 |
| WO | 9602792 A2 | | 2/1996 |
| WO | 02058818 A2 | | 8/2002 |
| WO | 03083015 A2 | | 10/2003 |
| WO | 2004074220 A1 | | 9/2004 |
| WO | 2009080621 A1 | | 7/2009 |
| WO | 2009121456 A1 | | 10/2009 |
| WO | 2010066281 A1 | | 6/2010 |
| WO | 2010079177 A2 | | 7/2010 |
| WO | 2010127752 A1 | | 11/2010 |
| WO | 2011021024 A1 | | 2/2011 |
| WO | 2011081836 A2 | | 7/2011 |
| WO | 2011090616 A2 | | 7/2011 |
| WO | 2012005862 A1 | | 1/2012 |
| WO | 2012108686 A2 | | 8/2012 |

OTHER PUBLICATIONS

Abedi, "Economic Analysis of a New Gas to Ethylene Technology", Thesis-Texas A&M University, May 2007.

Anvari, "Enhancement of 2,3-Butanediol Production by *Klebsiella oxytoca* PTCC 1402", Journal of Biomedicine and Biotechnology, 2011.

Barnard, "The pyrolysis of tert.-butanol", Trans. Faraday Soc., 1959, vol. 55, pp. 947-951.

Bartholome, "The BASF-process for production of acetylene by partial oxidation of gaseous hydrocarbons", Special Supplement to Chemical Engineering Science, 1954, pp. 94-104. vol. 3.

(56) References Cited

OTHER PUBLICATIONS

Bergeot, Simulated moving bed reactor for paraxylene production, Chemical Engineering Transactions, 2009, pp. 87-92, vol. 17.
Besev, "Radical Cyclization Approaches to Pyrrolidines", Acta Universitatis Upsaliensis, Uppsala University, 2002.
Biswas, "Enhanced production of 2,3-Butanediol by engineered *Bacillus subtilis*", Appl. Microbiol. Biotechnology, 2012, vol. 94, pp. 651-658.
Buhl, "Bio-Production of Light Olefins", ChemManager online, Europe, Mar. 19, 2012.
Cerff, "Supersonic Injection and Mixing in the Shock Wave Reactor", Thesis M.S. Aeronautics and Astronautics, University of Washington, 2010.
Chemsystems, "1,4-Butanediol/THF 98/99S1", Sep. 1999.
Chemsystems, "Acetylene Production Technologies Perp 05/06S9", Nexant, 2007.
Chemsystems, "Acrylic Acid Perp 08/09", Nexant, Aug. 2010.
Chemsystems, "Butadiene/Butylenes Perp 09/10-5", Nexant, Sep. 2010.
Chemsystems online, "Ethylene oxide/Ethylene Glycol", Nexant, 2009.
Chemsystems, "Green Propylene", Nexant, 2009.
Chemsystems, "Vinyl Chloride Monomer (VCM0/Ethylene Dichloride (EDC) Perp 08-09-4", Nexant, Oct. 2009.
Choudhury, "Thermal Decomposition of t-Butyl Alcohol in Shock Waves", Combustion Scienve and Technology, 1990, vol. 71, iss 4-6, pp. 219-232.
Collins, "Disproportionation of Toulene over ZSM-5 under Near-Critical Conditions", AlChe Journal, 1998, pp. 1211-1214, vol. 34, No. 7.
Fernandez, "A Noise-Temperature Measurement System Using a Cryogenic Attenuator", TMO Progress Report 42-135, 1998.
Garner, "Asymmetric Multicomponent [C+NC+CC] Synthesis of Highly Functionalized Pyrrolidines Catalyzed by Silver(I)", Organic Letters, 2006, pp. 3647-3650, vol. 8, No. 17.
Gorman, "Soluble, Highly Conjugated Derivatives of Polyacetylene from the Ring-Opening Metathesis Polymerization of Monosubstituted Cyclooctatetraenes: Synthesis and the Relationship between Polymer Structure and Physical Properties", Office of Naval Research, Technical Report 1, prepared for J. Am. Chem. Soc, 1993, vol. 115, pp. 1397-1409.
Hanika, "Catalytic Transalkylation of Trimethylbenzenes with Toulene", Petroleum and Coal, 2003. pp. 78-82, vol. 45, 1-2.
Hendriksen, "Intermediates to Ethylene Glycol: Carbonylation of Formaldehyde Catalyzed by Nafion Solid Perfluorosulfonic Acid Resin", Exxon Research and Engineering Company, 1983.
Hoener, "The Production and Characterization of Mid-Gap States in trans-Polyacetylene", Thesis Ph.D, University of California, Berkeley, Aug. 1998.
ISIS.com, "Caprolactam Production and Manufacturing Process", Chemical Report, Apr. 23, 2010.
Jui, "Enantioselective Organo-SOMO Cycloadditions: A Catalytic Approach to Complex Pyrrolidines from Olefins and Aldehydes", J. Am. Chem. So., 2012, pp. 11400-11403, vol. 134.
Kolts, "Enhanced Ethylene and Ethane Production with Free-Radical Cracking Catalysts", Science, May 1986, pp. 744-746, vol. 32.
Kopke, "2,3-Butanediol Production by Acetrogenic Bacteria, an Alternative Route to Chemical Synthesis, Using Industrial Waste Gas", Applied and Environmental Microbiology, 2011, pp. 5467-5475, vol. 77, No. 15.
Lim, "Production of Ethylbenzene from Benzene and Ethylene by Liquid-phase Alkylation Using Zeolite Catalysts", SRI Consulting, PEP Process Module, Oct. 1999.
Marcu, "Oxidative dehydrogenation of isobutane over a titanium pyrophosphate catalyst", J. Serb. Chem. Soc., 2005, pp. 791-798, vol. 70, 6.
Biochemistry Forum, "Three kinds of methyl acrylate production methods", Nature Network, Feb. 21, 2011.
Rep, "Side chain alkylation of toluene with methanol over basic zeolites—novel production route towards styrene?", Thesis-University of Twente, 2002.
Tai, "Temperature-controlled phase-transfer catalysis for ethylene glycol production from cellulose", Chem. Commun., 2012, pp. 7052-7054, vol. 48.
Takemoto, "Synthesis of Styrenes through the Biocatalytic Decarboxylation of trans-Cinnamic Acids by Plant Cell Cultures", Chem. Pharm. Bull., 2001, pp. 639-641, vol. 49, 5.
Towfighi, "Steam Cracking of Naptha in Packed Bed Reactors", Ind. Eng. Chem. Res., 2002, pp. 1419-1424, vol. 41.
Wang, "Review of Directly Producing Light Olefins via CO Hydrogenation", Journal of Natural Gas Chemistry, 2003, pp. 10-16, vol. 12.
White, "Novel Multistep Process for Production on N-Methyl-2-Pyrrolidone from Renewable Resources", Pacific Northwest National Laboratory, 2005.
Zimmermann, "Ethylene", Ullmann's Encyclopedia of Industrial Chemistry, Jun. 2000.
Zuidhof, "The Beckmann rearrangement of cyclohexanone oxime to ☐-caprolactam in micromixers and microchannels", Technische Universiteit Eindhoven, 2010.
U.S. Appl. No. 13/947,485, filed Jul. 22, 2013, Negiz et al.
U.S. Appl. No. 13/947,404, filed Jul. 22, 2013, Stevens et al.
U.S. Appl. No. 13/950,763, filed Jul. 25, 2013, Rende et al.
U.S. Appl. No. 13/925,115, filed Jun. 24, 2013, Rende et al.
U.S. Appl. No. 13/950,526, filed Jul. 25, 2013, Rende et al.
U.S. Appl. No. 13/941,631, filed Jul. 15, 2013, Rende et al.
U.S. Appl. No. 13/950,921, filed Jul. 25, 2013, Rende et al.
U.S. Appl. No. 13/950,886, filed Jul. 25, 2013, Rende et al.
U.S. Appl. No. 13/950,504, filed Jul. 25, 2013, Rende et al.
U.S. Appl. No. 13/950,475, filed Jul. 25, 2013, Rende et al.
U.S. Appl. No. 13/941,620, filed Jul. 15, 2013, Rende et al.
U.S. Appl. No. 13/942,676, filed Jul. 15, 2013, Rende et al.
U.S. Appl. No. 13/943,848, filed Jul. 17, 2013, Rende et al.
U.S. Appl. No. 13/943,845, filed Jul. 17, 2013, Rende et al.
U.S. Appl. No. 13/943,840, filed Jul. 17, 2013, Rende et al.
U.S. Appl. No. 13/942,871, filed Jul. 16, 2013, Rende et al.
U.S. Appl. No. 13/943,852, filed Jul. 17, 2013, Rende et al.
U.S. Appl. No. 13/942,682, filed Jul. 15, 2013, Rende et al.
U.S. Appl. No. 13/950,830, filed Jul. 25, 2013, Rende et al.
U.S. Appl. No. 13/943,856, filed Jul. 17, 2013, Rende et al.
U.S. Appl. No. 13/950,787, filed Jul. 25, 2013, Rende et al.
U.S. Appl. No. 13/966,367, filed Aug. 14, 2013, Bricker et al.
U.S. Appl. No. 13/915,143, filed Jun. 11, 2013, Bricker et al.
U.S. Appl. No. 13/915,151, filed Jun. 11, 2013, Bricker et al.
U.S. Appl. No. 13/915,020, filed Jun. 11, 2013, Bricker et al.
U.S. Appl. No. 13/915,159, filed Jun. 11, 2013, Bricker et al.
U.S. Appl. No. 13/915,057, filed Jun. 11, 2013, Bricker et al.
U.S. Appl. No. 13/915,099, filed Jun. 11, 2013, Bricker et al.
U.S. Appl. No. 13/915,106, filed Jun. 11, 2013, Bricker et al.
U.S. Appl. No. 13/915,113, filed Jun. 11, 2013, Bricker et al.
U.S. Appl. No. 13/915,130, filed Jun. 11, 2013, Bricker et al.
U.S. Appl. No. 13/966,544, filed Aug. 14, 2013, Bricker et al.
U.S. Appl. No. 13/967,459, filed Aug. 15, 2013, Rende et al.
U.S. Appl. No. 13/952,810, filed Jul. 29, 2013, Rende et al.
U.S. Appl. No. 13/916,913, filed Jun. 13, 2013, Bedard et al.
U.S. Appl. No. 13/967,327, filed Aug. 14, 2013, Bedard et al.
U.S. Appl. No. 13/966,961, filed Aug. 14, 2013, Bedard et al.
U.S. Appl. No. 13/966,752, filed Aug. 14, 2013, Bedard et al.
U.S. Appl. No. 13/964,458, filed Aug. 12, 2013, Bedard et al.
U.S. Appl. No. 13/964,486, filed Aug. 12, 2013, Bedard et al.
U.S. Appl. No. 13/964,396, filed Aug. 12, 2013, Bedard et al.
U.S. Appl. No. 13/964,498, filed Aug. 12, 2013, Bedard et al.
U.S. Appl. No. 13/916,924, filed Jun. 13, 2013, Bedard et al.
U.S. Appl. No. 13/916,936, filed Jun. 13, 2013, Bedard et al.
U.S. Appl. No. 13/967,373, filed Aug. 15, 2013, Bedard et al.
U.S. Appl. No. 13/967,334, filed Aug. 14, 2013, Bedard et al.
U.S. Appl. No. 13/967,404, filed Aug. 15, 2013, Bedard et al.
U.S. Appl. No. 13/967,397, filed Aug. 15, 2013, Bedard et al.
U.S. Appl. No. 13/967,391, filed Aug. 15, 2013, Bedard et al.
U.S. Appl. No. 13/967,428, filed Aug. 15, 2013, Bedard et al.
U.S. Appl. No. 13/967,440, filed Aug. 15, 2013, Bedard et al.

(56) References Cited

OTHER PUBLICATIONS

U.S. Appl. No. 13/967,533, filed Aug. 15, 2013, Bedard et al.
U.S. Appl. No. 13/967,674, filed Aug. 15, 2013, Bedard et al.
U.S. Appl. No. 13/964,524, filed Aug. 12, 2013, Bedard et al.
U.S. Appl. No. 13/967,697, filed Aug. 15, 2013, Bedard et al.
U.S. Appl. No. 13/967,792, filed Aug. 15, 2013, Bedard et al.
U.S. Appl. No. 13/964,411, filed Aug. 12, 2013, Towler et al.
U.S. Appl. No. 13/964,425, filed Aug. 12, 2013, Towler et al.
U.S. Appl. No. 13/916,966, filed Jun. 13, 2013, Bedard et al.
U.S. Appl. No. 13/967,741, filed Aug. 15, 2013, Towler et al.
Smidt et al., "The Oxidation of Olefins with Palladium Chloride Catalysts", Angew. Chem. Internatio. Edit., 1962, pp. 80-88, vol. 1, No. 2.
U.S. Appl. No. 13/947,519, filed Jul. 22, 2013, Negiz et al.
Beskov, "Chemical Technology and the Fundamentals of Industrial Ecology: Textbook for Universities", Moscow, Khimiya, 1999, p. 182-184.
Fischer, "Self-repairing material systems—a dream or a reality?", Natural Science, vol. 2, No. 8, 873-901 (2010).
Froggatt, "Nuclear Power: Myth and Reality", Dec. 2005, No. 2, Russian version, p. 24.
Knunyantsa, "Soviet Encyclopedia", G.A. Jagodin Publishing, Moscow, 1988, vol. 1, col. 209.
Knunyantsa, "Soviet Encyclopedia", G.A. Jagodin Publishing, Moscow, 1990, vol. 2, col. 249-250.
Knunyantsa, "Great Russian Encyclopedia", Scientific Publishing, Moscow, 1992, vol. 3, col. 649-650.
Knunyantsa "Soviet Encyclopedia", G.A. Jagodin Publishing, Moscow, 1988, vol. 1, col. 931.
Lefevr, "Processes in Combustion Chambers", MIR, Moscow, 1986, p. 317-323.
Matar, "Chemistry of Petrochemical Processes" Second Edition, Provides Quick and Easy Access to Hundreds of Reactions, Processes and Products, 1994, 2000 by Gulf Publishing Company, Houston, Texas, p. 392, p. 214, last paragraph, p. 95, p. 94, Figs. 3-12, p. 246-248, p. 206, lines 8-11, p. 209-210, p. 247, paragraph 1, p. 205-206, p. 33-34, p. 91, paragraph 1.
Nikitin, book "Brief Guidelines of Gas Welder and Burner", 1960, p. 24.
Novoselov, "Electric Field Effect in Atomically Thin Carbon Films", Science 306, 666-669 (2004).
Reed, "The Superalloys: Fundamentals and Applications", Cambridge University Press, 2006, p. 1.
Shah, Ullmann's Encyclopedia of Industrial Chemistry, 2007, Heat Exchange, p. 14-17, 27, 31, 46-48.
Zolotova, "Great Russian Encyclopedia", Scientific Publishing, Moscow, 1992, vol. 3, col. 5-8.
Laukhuf, "Adsorption of Carbon Dioxide, Acetylene, Ethane, and Propylene on Charcoal at Near Room Temperatures", Journal of Chemical and Engineering Data, vol. 14, No. 1, Jan. 1969, p. 48-51.
Ren, "Olefins from conventional and heavy feedstocks: Energy use in steam cracking and alternative processes", Energy 31 (2006) 425-451.
Search Report dated Jan. 10, 2014 for corresponding PCT Appl. No. PCT/US2013/047741.

\* cited by examiner

US 9,023,255 B2

PRODUCTION OF NITROGEN COMPOUNDS FROM A METHANE CONVERSION PROCESS

CROSS-REFERENCE TO RELATED APPLICATION

This application claims priority from Provisional Application No. 61/691,371 filed Aug. 21, 2012, the contents of which are hereby incorporated by reference in its entirety.

FIELD OF THE INVENTION

A process is disclosed for producing chemicals useful for the production of polymers from the conversion of methane to acetylene using a supersonic flow reactor. More particularly, the process is for the production of pyridines.

BACKGROUND OF THE INVENTION

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers are light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

A principal means of production is the cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production. In a typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier by-products that tend to foul the pyrolysis tube walls. However, there is little room left to improve the residence times or overall energy consumption in tradition pyrolysis processes.

More recent attempts to decrease light olefin production costs include utilizing alternative processes and/or feedstreams. In one approach, hydrocarbon oxygenates and more specifically methanol or dimethylether (DME) are used as an alternative feedstock for producing light olefin products. Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once the oxygenates are formed, the process includes catalytically converting the oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. U.S. Pat. No. 4,587,373 discloses using a zeolitic catalyst like ZSM-5 for purposes of making light olefins. U.S. Pat. Nos. 5,095,163; 5,126,308 and 5,191,141 on the other hand, disclose an MTO conversion technology utilizing a non-zeolitic molecular sieve catalytic material, such as a metal aluminophosphate (ELAPO) molecular sieve. OTO and MTO processes, while useful, utilize an indirect process for forming a desired hydrocarbon product by first converting a feed to an oxygenate and subsequently converting the oxygenate to the hydrocarbon product. This indirect route of production is often associated with energy and cost penalties, often reducing the advantage gained by using a less expensive feed material. In addition, some oxygenates, such as vinyl acetate or acrylic acid, are also useful chemicals and can be used as polymer building blocks.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel. While this method may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

While the foregoing traditional pyrolysis systems provide solutions for converting ethane and propane into other useful hydrocarbon products, they have proven either ineffective or uneconomical for converting methane into these other products, such as, for example ethylene. While MTO technology is promising, these processes can be expensive due to the indirect approach of forming the desired product. Due to continued increases in the price of feeds for traditional processes, such as ethane and naphtha, and the abundant supply and corresponding low cost of natural gas and other methane sources available, for example the more recent accessibility of shale gas, it is desirable to provide commercially feasible and cost effective ways to use methane as a feed for producing ethylene and other useful hydrocarbons.

SUMMARY OF THE INVENTION

A method for producing acetylene according to one aspect is provided. The method generally includes introducing a feed stream portion of a hydrocarbon stream including methane into a supersonic reactor. The method also includes pyrolyzing the methane in the supersonic reactor to form a reactor effluent stream portion of the hydrocarbon stream including acetylene. The method further includes treating at least a portion of the hydrocarbon stream in a process for producing higher value products.

In one embodiment, the process of the present invention utilizes the acetylene generated by the reactor above to produce pyridines. The acetylene stream and an ammonia stream are passed to a second reactor to generate an effluent stream comprising pyridines.

In one aspect of this invention, the use of ammonia is an important chemical precursor for the production of nitrogen based compounds. Ammonia production is energy intensive, and the present process integrate the large amount of heat generated by the supersonic reactor into the production of ammonia. The process includes the generation of acetylene as above, along with a large amount waste heat. The acetylene effluent stream is passed to a separation unit to generate a first stream comprising acetylene and a second stream comprising hydrogen. The second stream, a nitrogen stream and the heat from the reactor are passed to an ammonia reactor to generate an ammonia effluent stream.

Other objects, advantages and applications of the present invention will become apparent to those skilled in the art from the following detailed description and drawings.

DETAILED DESCRIPTION OF THE INVENTION

Figure 1:
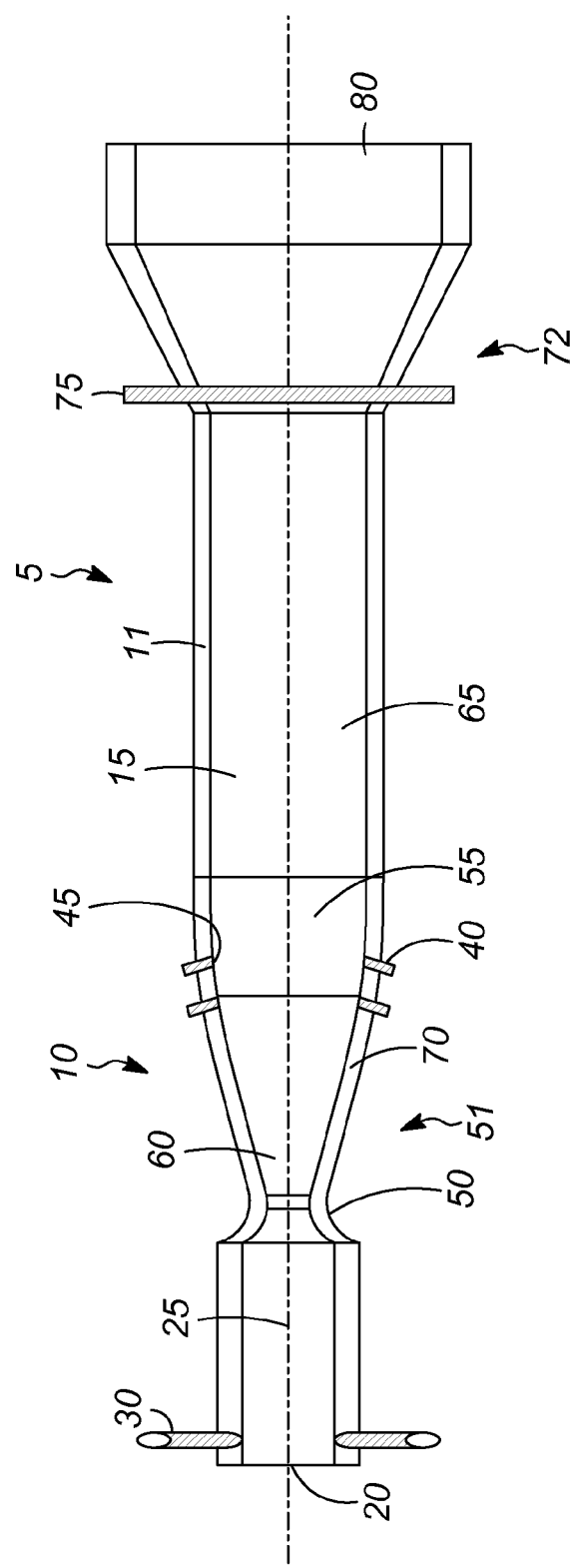
FIG. 1 is a side cross-sectional view of a supersonic reactor in accordance with various embodiments described herein.

One proposed alternative to the previous methods of producing hydrocarbon products that has not gained much commercial traction includes passing a hydrocarbon feedstock into a supersonic reactor and accelerating it to supersonic speed to provide kinetic energy that can be transformed into heat to enable an endothermic pyrolysis reaction to occur. Variations of this process are set out in U.S. Pat. Nos. 4,136, 015 and 4,724,272, and Russian Patent No. SU 392723A. These processes include combusting a feedstock or carrier fluid in an oxygen-rich environment to increase the temperature of the feed and accelerate the feed to supersonic speeds. A shock wave is created within the reactor to initiate pyrolysis or cracking of the feed. In particular, the hydrocarbon feed to the reactor comprises a methane feed. The methane feed is reacted to generate an intermediate process stream which is then further processed to generate a hydrocarbon product stream. Particular hydrocarbon product streams of interest are nitrogen based hydrocarbons such as pyridines.

More recently, U.S. Pat. Nos. 5,219,530 and 5,300,216 have suggested a similar process that utilizes a shock wave reactor to provide kinetic energy for initiating pyrolysis of natural gas to produce acetylene. More particularly, this process includes passing steam through a heater section to become superheated and accelerated to a nearly supersonic speed. The heated fluid is conveyed to a nozzle which acts to expand the carrier fluid to a supersonic speed and lower temperature. An ethane feedstock is passed through a compressor and heater and injected by nozzles to mix with the supersonic carrier fluid to turbulently mix together at a Mach 2.8 speed and a temperature of about 427° C. The temperature in the mixing section remains low enough to restrict premature pyrolysis. The shockwave reactor includes a pyrolysis section with a gradually increasing cross-sectional area where a standing shock wave is formed by back pressure in the reactor due to flow restriction at the outlet. The shock wave rapidly decreases the speed of the fluid, correspondingly rapidly increasing the temperature of the mixture by converting the kinetic energy into heat. This immediately initiates pyrolysis of the ethane feedstock to convert it to other products. A quench heat exchanger then receives the pyrolyzed mixture to quench the pyrolysis reaction.

Methods and systems for converting hydrocarbon components in methane feed streams using a supersonic reactor are generally disclosed. As used herein, the term "methane feed stream" includes any feed stream comprising methane. The methane feed streams provided for processing in the supersonic reactor generally include methane and form at least a portion of a process stream that includes at least one contaminant. The methods and systems presented herein remove or convert the contaminant in the process stream and convert at least a portion of the methane to a desired product hydrocarbon compound to produce a product stream having a reduced contaminant level and a higher concentration of the product hydrocarbon compound relative to the feed stream. By one approach, a hydrocarbon stream portion of the process stream includes the contaminant and methods and systems presented herein remove or convert the contaminant in the hydrocarbon stream.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such hydrocarbon stream. The "hydrocarbon stream" may include the methane feed stream, a supersonic reactor effluent stream, a desired product stream exiting a downstream hydrocarbon conversion process or any intermediate or by-product streams formed during the processes described herein. The hydrocarbon stream may be carried via a process stream line 115, which includes lines for carrying each of the portions of the process stream described above. The term "process stream" as used herein includes the "hydrocarbon stream" as described above, as well as it may include a carrier fluid stream, a fuel stream, an oxygen source stream, or any streams used in the systems and the processes described herein. The process stream may be carried via a process stream line 115, which includes lines for carrying each of the portions of the process stream described above.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offers significant improvement over traditional pyrolysis processes. It has more recently been realized that these processes may also be able to convert methane to acetylene and other useful hydrocarbons, whereas more traditional pyrolysis processes were incapable or inefficient for such conversions.

The majority of previous work with supersonic reactor systems, however, has been theoretical or research based, and thus has not addressed problems associated with practicing the process on a commercial scale. In addition, many of these prior disclosures do not contemplate using supersonic reactors to effectuate pyrolysis of a methane feed stream, and tend to focus primarily on the pyrolysis of ethane and propane. One problem that has recently been identified with adopting the use of a supersonic flow reactor for light alkane pyrolysis, and more specifically the pyrolysis of methane feeds to form acetylene and other useful products therefrom, includes negative effects that particular contaminants in commercial feed streams can create on these processes and/or the products produced therefrom. Previous work has not considered the need for product purity, especially in light of potential downstream processing of the reactor effluent stream. Product purity can include the separation of several products into separate process streams, and can also include treatments for removal of contaminants that can affect a downstream reaction, and downstream equipment.

In accordance with various embodiments disclosed herein, therefore, processes and systems for converting the methane to a product stream are presented. The methane is converted to an intermediate process stream comprising acetylene. The intermediate process stream is converted to a second process stream comprising either a hydrocarbon product, or a second intermediate hydrocarbon compound. The processing of the intermediate acetylene stream can include purification or separation of acetylene from by-products.

The removal of particular contaminants and/or the conversion of contaminants into less deleterious compounds has been identified to improve the overall process for the pyrolysis of light alkane feeds, including methane feeds, to acetylene and other useful products. In some instances, removing these compounds from the hydrocarbon or process stream has been identified to improve the performance and functioning of the supersonic flow reactor and other equipment and processes within the system. Removing these contaminants from hydrocarbon or process streams has also been found to reduce poisoning of downstream catalysts and adsorbents used in the process to convert acetylene produced by the supersonic reactor into other useful hydrocarbons, for example hydrogenation catalysts that may be used to convert acetylene into ethylene. Still further, removing certain contaminants from a hydrocarbon or process stream as set forth herein may facilitate meeting product specifications.

In accordance with one approach, the processes and systems disclosed herein are used to treat a hydrocarbon process stream, to remove a contaminant therefrom and convert at least a portion of methane to acetylene. The hydrocarbon process stream described herein includes the methane feed stream provided to the system, which includes methane and may also include ethane or propane. The methane feed stream may also include combinations of methane, ethane, and propane at various concentrations and may also include other hydrocarbon compounds. In one approach, the hydrocarbon feed stream includes natural gas. The natural gas may be provided from a variety of sources including, but not limited to, gas fields, oil fields, coal fields, fracking of shale fields, biomass, and landfill gas. In another approach, the methane feed stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The methane feed stream may include a stream from combinations of different sources as well.

In accordance with the processes and systems described herein, a methane feed stream may be provided from a remote location or at the location or locations of the systems and methods described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation methods. For example a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 65 mol-% to about 100 mol-%. In another example, the concentration of methane in the hydrocarbon feed ranges from about 80 mol-% to about 100 mol-% of the hydrocarbon feed. In yet another example, the concentration of methane ranges from about 90 mol-% to about 100 mol-% of the hydrocarbon feed.

In one example, the concentration of ethane in the methane feed ranges from about 0 mol-% to about 35 mol-% and in another example from about 0 mol-% to about 10 mol-%. In one example, the concentration of propane in the methane feed ranges from about 0 mol-% to about 5 mol-% and in another example from about 0 mol-% to about 1 mol-%.

The methane feed stream may also include heavy hydrocarbons, such as aromatics, paraffinic, olefinic, and naphthenic hydrocarbons. These heavy hydrocarbons if present will likely be present at concentrations of between about 0 mol-% and about 100 mol-%. In another example, they may be present at concentrations of between about 0 mol-% and 10 mol-% and may be present at between about 0 mol-% and 2 mol-%.

The present invention provides a method of producing pyridine from methane. The process includes converting the methane through a pyrolysis reaction in a supersonic reactor to generate an effluent stream comprising acetylene. The acetylene stream is passed with a second stream comprising ammonia to a second reactor operated at second reaction conditions to generate a second effluent stream comprising pyridine. The second reactor is operated with a catalyst and at a temperature less than 350° C. Catalysts useful for the process in the second reactor include metals on a support. Metals for the catalysis include, but are not limited to, lead, cadmium, bismuth, gold, and combinations of metals. The ratio of acetylene to ammonia is greater than 2 and a stoichiometric amount is about 3 to 1. In a variation, acetylene can be reacted with ammonia to form a nitrile. The nitrile is then reacted with more acetylene to generate a pyridine compounds. The reaction can be thermally induced through high temperatures and pressures, or can be photoinduced at lower temperatures and pressures.

Another set of reaction conditions in the second reactor include a temperature in the range from 50° C. to 600° C., wherein the reaction in the second reactor is carried out over a metal chloride catalyst. Catalyst include zinc chloride, cadmium chloride, lead chloride, ferric chloride, stannous chloride and combinations of metal chlorides. The catalyst can further include promoter compounds, wherein the promoters are selected from alkali chlorides or alkaline earth chlorides. Preferred promoter compounds include potassium chloride and/or sodium chloride.

The process can further include passing the second effluent stream comprising pyridine to a pyridine purification unit to generate a pyridine product stream and a methane effluent stream. The methane effluent stream can be passed back to the methane stream that is fed to the supersonic reactor, for increasing the conversion of methane.

In one embodiment, the present invention includes a process for the production of methyl cyanide. The method includes generating an acetylene stream through the pyrolysis of methane in a supersonic reactor to generate an effluent stream comprising acetylene. The acetylene is passed to a hydrotreating reactor to generate a hydrotreating reactor effluent comprising ethylene. The ethylene effluent stream and an ammonia stream is passed to a methyl cyanide reactor, and an effluent stream having methyl cyanide is generated. The operation of the methyl cyanide reactor includes a molar feed ratio of ethylene to ammonia in the range from 0.5 to 2.0.

An aspect of the present invention is the co-production of ammonia. The ammonia can be processed for subsequent processes to generate nitrogen based compounds, or for distribution as ammonia. The production of ammonia requires high temperatures to obtain satisfactory yields. Ammonia production is important for a wide range of chemicals, especially fertilizers, which can consume as much as 1 to 2% of world wide fossil fuel energy consumption. The present invention utilizes the large amount of heat at high temperature generated in the supersonic reactor to produce ammonia for the generation of downstream chemicals where ammonia is a precursor. The process includes recovering hydrogen from reactor effluent stream and passing the hydrogen with a source of nitrogen to an ammonia reactor. The heat for the ammonia reactor can be supplied by the supersonic reactor through known heat transfer means. The heat can also be passed to the reactor through passing the hydrogen and nitrogen feedstreams through heating coils, either in or surrounding the reaction chamber of the supersonic reactor.

The method for ammonia production, and heat recovery includes reacting a methane feed in a supersonic reactor to convert the methane to acetylene in an effluent stream. The effluent stream is passed to a separation unit to generate a first stream comprising acetylene, and a second stream comprising hydrogen. The second stream and a nitrogen stream are passed to an ammonia reactor, where heat is supplied from the supersonic reactor.

The ammonia reactor includes a catalyst, and is operated at a temperature between 300° C. and 550° C. The ammonia reactor conditions include a pressure between 15 and 25 MPa, and the nitrogen source can be air, or a nitrogen enriched source. The catalyst in the ammonia reactor includes a metal or metal oxide on a support. The metal, or metal oxide, can be selected from iron, osmium, or ruthenium, and can also include a mixture of metals. The catalyst can also include a promoter, wherein the promoter is selected from $K_2O$, CaO, $SiO_2$, and $Al_2O_3$. The promoter can also be a part of the support, or can be a mixture added to the metal or metal oxide on a support.

In one embodiment, the invention provides for the production if pyrolidines. The process includes the generation of acetylene, as described above. The acetylene stream is passed to a dimerization reactor, operated at dimerization reaction conditions to form a second effluent stream comprising butenes and butynes. The second effluent stream and an ammonia feed stream is passed to an amine reactor operated at amine reactor conditions to generate an amine reactor effluent stream comprising t-butyl amine. The amine reactor effluent stream is passed to a cyclization reactor to form a cyclization stream comprising pyrrolidine. In one aspect of this embodiment, the acetylene stream is passed to a hydrogenation reactor to generate a stream comprising ethylene, with the ethylene stream passed to the dimerization reactor to generate an effluent stream comprising butenes. The butenes are then reacted with ammonia to generate an amine stream.

In one embodiment, the pyrolidine stream is passed to an oxidation reactor to convert the pyrolidines to pyrolidones.

In another embodiment, the invention includes a process for the production of caprolactam. Caprolactam is a precursor for the production of nylon. The method of producing caprolactam can take several different paths. One such path includes the production of acetylene to generate an acetylene stream. The acetylene is converted in a hydrogenation reactor to ethylene. The ethylene is dimerized in a dimerization reactor to generate an effluent stream comprising butadienes. The dimerization stream comprising butadienes is passed with carbon monoxide and methanol to a fourth reactor for carbonylation to generate a fourth effluent stream comprising methyl pentenoate. The fourth effluent stream is passed to a hydroformylation reactor to generate a hydroformylation effluent stream comprising methyl formylvalerate. The methyl formylvalerate is passed to a sixth reactor to generate and effluent stream comprising aminocaproate, and the methyl aminocaproate stream to a seventh reactor to form a sixth effluent stream comprising caprolactam. The process further includes passing hydrogen and ammonia to the sixth reactor.

The carbonylation reactor uses a catalyst for carrying out the reaction. In one embodiment, the catalyst is a palladium salt catalyst. In another embodiment, the catalyst is a ruthenium metal on a support, wherein the support can be alumina.

The hydroformylation reactor uses a catalyst in the hydroformylation process. Catalysts include phosphine based materials.

In another embodiment for carprolactam production, the process includes generating an acetylene stream as above. The acetylene stream is passed to a second reactor for generating an effluent stream comprising cyclohexanone. The cyclohexanone is converted in a third reactor to generate a third effluent stream comprising cyclohexanone oxine. The cyclohexanone oxine is then converted in a fourth reactor to generate a fourth effluent stream comprising caprolactam. In one aspect of this embodiment, the acetylene is first passed to a reactor co generate an effluent stream comprising cyclohexanol, and the cyclohexanol stream is passed to a fifth reactor to generate the cyclohexanone stream, with the cyclohexanone stream passed to the third reactor.

The third reactor includes a second feed stream comprising hydroxylamine, and the fourth reactor includes an acid for the conversion a cyclohexanone oxine to caprolactam. One preferred acid is sulfuric acid ($H_2SO_4$).

In yet another embodiment for the production of caprolactam, the process includes the production of acetylene as above. The acetylene is passed to a polymerization reactor to generate an effluent stream comprising polyacetylenes. The polyacetylene stream is passed to an aromatization reactor to generate an effluent stream comprising toluene. The toluene stream is passed to an oxidation reactor to generate an effluent stream having benzoic acid. The benzoic acid stream is passed to a hydrogenation reactor to generate a fourth process stream comprising cyclohexanecarboxylic acid. The cyclohexanecarboxylic acid stream is passed to a caprolactam reactor at a temperature between 70° C. and 100° C. with a nitrosyl-sulfuric to generate an effluent stream comprising caprolactam.

The oxidation reaction conditions in the oxidation reactor include a temperature between 150° C. to 200° C. and a pressure between 800 kPa and 1 MPa. The oxidation process is carried out over a cobalt catalyst.

The hydrogenation reaction conditions include a temperature between 100° C. and 300° C. and a pressure between 1 MPa and 2 MPa. The hydrogenation reaction is carried out over a catalytic metal on a support.

The process for forming acetylene from the methane feed stream described herein utilizes a supersonic flow reactor for pyrolyzing methane in the feed stream to form acetylene. The supersonic flow reactor may include one or more reactors capable of creating a supersonic flow of a carrier fluid and the methane feed stream and expanding the carrier fluid to initiate the pyrolysis reaction. In one approach, the process may include a supersonic reactor as generally described in U.S. Pat. No. 4,724,272, which is incorporated herein by reference, in their entirety. In another approach, the process and system may include a supersonic reactor such as described as a "shock wave" reactor in U.S. Pat. Nos. 5,219,530 and 5,300,216, which are incorporated herein by reference, in their entirety. In yet another approach, the supersonic reactor described as a "shock wave" reactor may include a reactor such as described in "Supersonic Injection and Mixing in the Shock Wave Reactor" Robert G. Cerff, University of Washington Graduate School, 2010.

While a variety of supersonic reactors may be used in the present process, an exemplary reactor 5 is illustrated in FIG. 1. Referring to FIG. 1, the supersonic reactor 5 includes a reactor vessel 10 generally defining a reactor chamber 15. While the reactor 5 is illustrated as a single reactor, it should be understood that it may be formed modularly or as separate vessels. A combustion zone or chamber 25 is provided for combusting a fuel to produce a carrier fluid with the desired temperature and flowrate. The reactor 5 may optionally include a carrier fluid inlet 20 for introducing a supplemental carrier fluid into the reactor. One or more fuel injectors 30 are provided for injecting a combustible fuel, for example hydrogen, into the combustion chamber 25. The same or other injectors may be provided for injecting an oxygen source into the combustion chamber 25 to facilitate combustion of the fuel. The fuel and oxygen are combusted to produce a hot carrier fluid stream typically having a temperature of from about 1200° C. to about 3500° C. in one example, between about 2000° C. and about 3500° C. in another example, and between about 2500° C. and 3200° C. in yet another example. According to one example the carrier fluid stream has a pressure of about 100 kPa or higher, greater than about 200 kPa in another example, and greater than about 400 kPa in another example.

The hot carrier fluid stream from the combustion zone 25 is passed through a converging-diverging nozzle 50 to accelerate the flowrate of the carrier fluid to above about mach 1.0 in one example, between about mach 1.0 and mach 4.0 in another example, and between about mach 1.5 and 3.5 in another example. In this regard, the residence time of the fluid in the reactor portion of the supersonic flow reactor is between about 0.5 to 100 ms in one example, about 1 to 50 ms in another example, and about 1.5 to 20 ms in another example.

A feedstock inlet 40 is provided for injecting the methane feed stream into the reactor 5 to mix with the carrier fluid. The feedstock inlet 40 may include one or more injectors 45 for injecting the feedstock into the nozzle 50, a mixing zone 55, an expansion zone 60, or a reaction zone or chamber 65. The injector 45 may include a manifold, including for example a plurality of injection ports.

In one approach, the reactor 5 may include a mixing zone 55 for mixing of the carrier fluid and the feed stream. In another approach, no mixing zone is provided, and mixing may occur in the nozzle 50, expansion zone 60, or reaction zone 65 of the reactor 5. An expansion zone 60 includes a diverging wall 70 to produce a rapid reduction in the velocity of the gases flowing therethrough, to convert the kinetic energy of the flowing fluid to thermal energy to further heat the stream to cause pyrolysis of the methane in the feed, which may occur in the expansion section 60 and/or a downstream reaction section 65 of the reactor. The fluid is quickly quenched in a quench zone 72 to stop the pyrolysis reaction from further conversion of the desired acetylene product to other compounds. Spray bars 75 may be used to introduce a quenching fluid, for example water or steam into the quench zone 72.

The reactor effluent exits the reactor via outlet 80 and as mentioned above forms a portion of the hydrocarbon stream. The effluent will include a larger concentration of acetylene than the feed stream and a reduced concentration of methane relative to the feed stream. The reactor effluent stream may also be referred to herein as an acetylene stream as it includes an increased concentration of acetylene. The acetylene may be an intermediate stream in a process to form another hydrocarbon product or it may be further processed and captured as an acetylene product stream. In one example, the reactor effluent stream has an acetylene concentration prior to the addition of quenching fluids ranging from about 2 mol-% to about 30 mol-%. In another example, the concentration of acetylene ranges from about 5 mol-% to about 25 mol-% and from about 8 mol-% to about 23 mol-% in another example.

In one example, the reactor effluent stream has a reduced methane content relative to the methane feed stream ranging from about 15 mol-% to about 95 mol-%. In another example, the concentration of methane ranges from about 40 mol-% to about 90 mol-% and from about 45 mol-% to about 85 mol-% in another example.

In one example the yield of acetylene produced from methane in the feed in the supersonic reactor is between about 40% and about 95%. In another example, the yield of acetylene produced from methane in the feed stream is between about 50% and about 90%. Advantageously, this provides a better yield than the estimated 40% yield achieved from previous, more traditional, pyrolysis approaches.

The invention can include an acetylene enrichment unit having an inlet in fluid communication with the reactor outlet, and an outlet for a acetylene enriched effluent. One aspect of the system can further include a contaminant removal zone having an inlet in fluid communication with the acetylene enrichment zone outlet, and an outlet in fluid communication with the hydrocarbon conversion zone inlet, for removing contaminants that can adversely affect downstream catalysts and processes. One contaminant to be removed is CO to a level of less than 0.1 mole %, and preferably to a level of less than 100 ppm by vol. An additional aspect of the invention is where the system can include a second contaminant removal zone having an inlet in fluid communication with the methane feed stream and an outlet in fluid communication with the supersonic reactor inlet.

By one approach, the reactor effluent stream is reacted to form another hydrocarbon compound. In this regard, the reactor effluent portion of the hydrocarbon stream may be passed from the reactor outlet to a downstream hydrocarbon conversion process for further processing of the stream. While it should be understood that the reactor effluent stream may undergo several intermediate process steps, such as, for example, water removal, adsorption, and/or absorption to provide a concentrated acetylene stream, these intermediate steps will not be described in detail herein.

Figure 2:
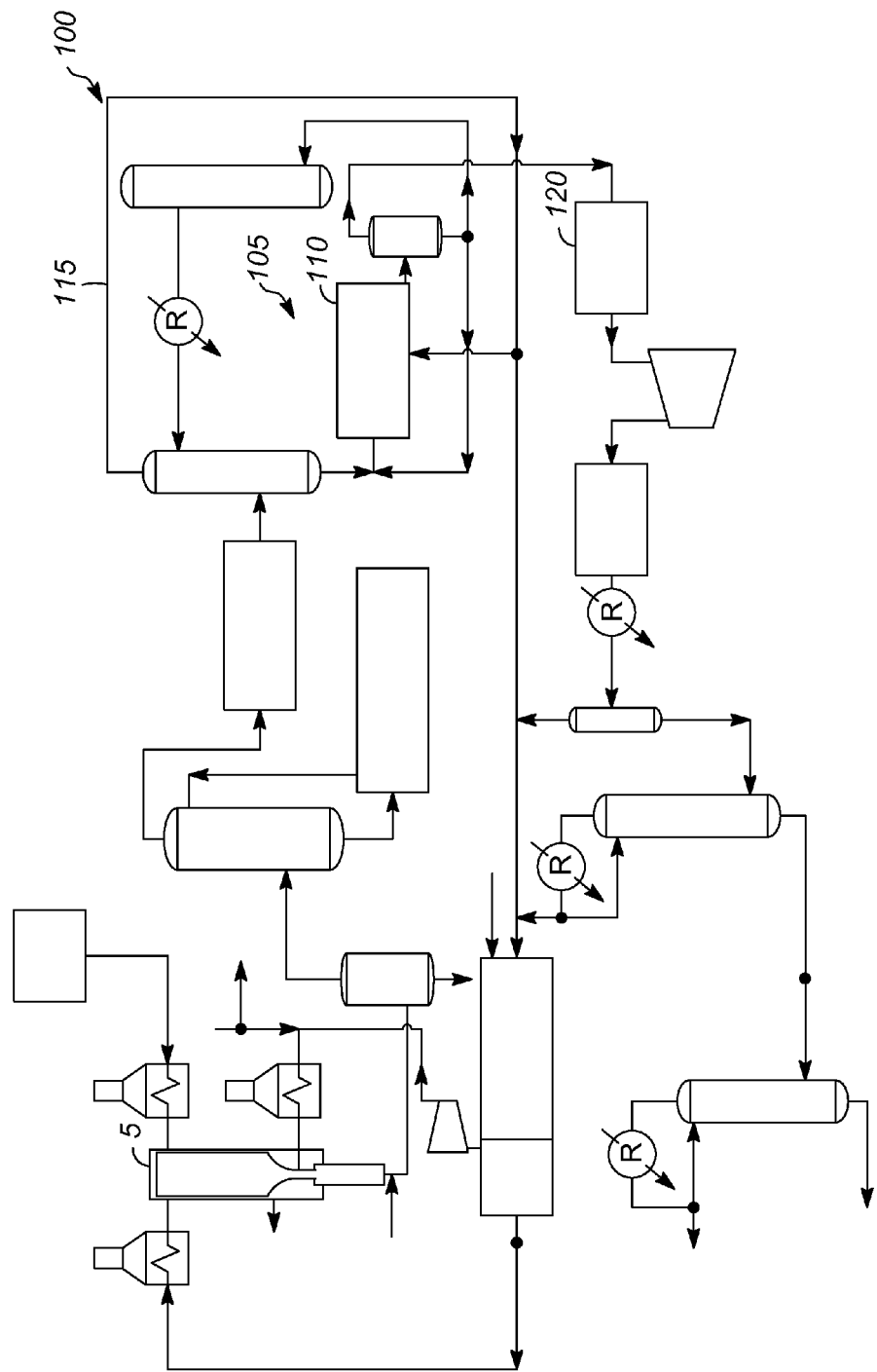
FIG. 2 is a schematic view of a system for converting methane into acetylene and other hydrocarbon products in accordance with various embodiments described herein.

Referring to FIG. 2, the reactor effluent stream having a higher concentration of acetylene may be passed to a downstream hydrocarbon conversion zone 100 where the acetylene may be converted to form another hydrocarbon product. The hydrocarbon conversion zone 100 may include a hydrocarbon conversion reactor 105 for converting the acetylene to another hydrocarbon product. While FIG. 2 illustrates a process flow diagram for converting at least a portion of the acetylene in the effluent stream to ethylene through hydrogenation in hydrogenation reactor 110, it should be understood that the hydrocarbon conversion zone 100 may include a variety of other hydrocarbon conversion processes instead of or in addition to a hydrogenation reactor 110, or a combination of hydrocarbon conversion processes. Similarly, it illustrated in FIG. 2 may be modified or removed and are shown for illustrative purposes and not intended to be limiting of the processes and systems described herein. Specifically, it has been identified that several other hydrocarbon conversion processes, other than those disclosed in previous approaches, may be positioned downstream of the supersonic reactor 5, including processes to convert the acetylene into other hydrocarbons, including, but not limited to: alkenes, alkanes, methane, acrolein, acrylic acid, acrylates, acrylamide, aldehydes, polyacetylides, benzene, toluene, styrene, aniline, cyclohexanone, caprolactam, propylene, butadiene, butyne diol, butandiol, C2-C4 hydrocarbon compounds, ethylene glycol, diesel fuel, diacids, diols, pyrrolidines, and pyrrolidones.

A contaminant removal zone 120 for removing one or more contaminants from the hydrocarbon or process stream may be located at various positions along the hydrocarbon or process stream depending on the impact of the particular contaminant on the product or process and the reason for the contaminants removal, as described further below. For example, particular contaminants have been identified to interfere with the operation of the supersonic flow reactor 5 and/or to foul components in the supersonic flow reactor 5. Thus, according to one approach, a contaminant removal zone is positioned upstream of the supersonic flow reactor in order to remove these contaminants from the methane feed stream prior to introducing the stream into the supersonic reactor. Other contaminants have been identified to interfere with a downstream processing step or hydrocarbon conversion process, in which case the contaminant removal zone may be positioned upstream of the supersonic reactor or between the supersonic reactor and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the hydrocarbon or process stream. In still other approaches, a contaminant removal zone may overlap or be integrated with another process within the system, in which case the contaminant may be removed during another portion of the process, including, but not limited to the supersonic reactor 5 or the downstream hydrocarbon conversion zone 100. This may be accomplished with or without modification to these particular zones, reactors or processes. While the contaminant removal zone 120 illustrated in FIG. 2 is shown positioned downstream of the hydrocarbon conversion reactor 105, it should be understood that the contaminant removal zone 120 in accordance herewith may be positioned upstream of the supersonic flow reactor 5, between the supersonic flow reactor 5 and the hydrocarbon conversion zone 100, or downstream of the hydrocarbon conversion zone 100 as illustrated in FIG. 2 or along other streams within the process stream, such as, for example, a carrier fluid stream, a fuel stream, an oxygen source stream, or any streams used in the systems and the processes described herein.

While there have been illustrated and described particular embodiments and aspects, it will be appreciated that numerous changes and modifications will occur to those skilled in the art, and it is intended in the appended claims to cover all those changes and modifications which fall within the true spirit and scope of the present disclosure and appended claims.

The invention claimed is:

1. A method for producing pyridine comprising:
   introducing a feed stream comprising methane into a supersonic reactor;
   pyrolyzing the methane in the supersonic reactor to pyrolyze the methane and to form a reactor effluent stream comprising acetylene; and
   passing the reactor effluent stream and a second stream comprising ammonia to a second reactor at second reaction conditions to form a second effluent stream comprising pyridine, wherein the second reaction conditions include a catalyst wherein the catalyst comprises a metal chloride.

2. The method of claim 1, wherein pyrolyzing the methane includes accelerating a hydrocarbon stream to a velocity of between about mach 1.0 and about mach 4.0 and slowing down the hydrocarbon stream to increase the temperature of the hydrocarbon process stream.

3. The method of claim 1, wherein pyrolyzing the methane includes heating the methane to a temperature of between about 1200° C. and about 3500° C. for a residence time of between about 0.5 ms and about 100 ms.

4. The method of claim 1, further comprising treating the reactor effluent stream to remove CO to a level below about 100 ppm by vol. of the reactor effluent stream.

5. The method of claim 2, wherein the hydrocarbon stream includes a methane feed stream portion upstream of the supersonic reactor comprising natural gas.

6. The method of claim 1 further comprising passing the second effluent stream to a pyridine purification unit to generate a pyridine product stream and a methane effluent stream.

7. The method of claim 6 further comprising passing the methane effluent stream to the feed stream to the supersonic reactor.

8. The method of claim 1 wherein the second reaction conditions include a temperature between 50° C. and 600° C.

9. The method of claim 1 wherein the catalyst is selected from the group consisting of zinc chloride, cadmium chloride, lead chloride, ferric chloride, stannous chloride, and mixtures thereof.

10. The method of claim 9 wherein the catalyst further comprises a compound from the group consisting of potassium chloride, sodium chloride, and mixtures thereof.

11. The method of claim 1 wherein the second reactor is operated with a catalyst, and wherein the catalyst is a metal chloride and the metal is selected from the group consisting of lead, cadmium, bismuth, gold, and mixtures thereof.

12. The method of claim 1 wherein the second reactor is operated at a temperature of less than 350° C.

\* \* \* \* \*